United States Patent [19]

Yamaguchi et al.

[11] 4,412,809
[45] Nov. 1, 1983

[54] OXYGEN DENSITY DETECTING DEVICE IN COMBUSTOR

[75] Inventors: Hiroshi Yamaguchi; Takashi Sekiguchi; Hideyuki Tsukahara; Nobumasa Negishi; Kisuke Fujita, all of Gunma, Japan

[73] Assignee: Mitsubishi Denki Kabushiki Kaisha, Tokyo, Japan

[21] Appl. No.: 277,504

[22] Filed: Jun. 26, 1981

[30] Foreign Application Priority Data

Jul. 1, 1980 [JP] Japan ................................. 55-89474

[51] Int. Cl.$^3$ ............................................... F23N 5/24
[52] U.S. Cl. ...................................... 431/76; 431/37; 431/208; 328/6; 340/579
[58] Field of Search ..................... 431/25, 75, 76, 208, 431/37, 41; 236/15 E; 422/54; 340/579; 328/1, 6

[56] References Cited

U.S. PATENT DOCUMENTS 3,049,409  8/1962  Dower .................................. 422/54
3,879,667  4/1975  Kraty et al. ............................ 328/6
4,032,286  6/1977  Kobayashi et al. ................... 431/76

Primary Examiner—Lee E. Barrett
Attorney, Agent, or Firm—Sughrue, Mion, Zinn, Macpeak and Seas

[57] ABSTRACT

An oxygen density detecting device for a combustor in which individual adjustment of reference levels for each combustor is not necessary. A memory device stores a reference ion current value from a sensor disposed in the combustor for a predetermined period of time extending from the time instant at which combustion breaks out in the combustor until the ion current has substantially stabilized. The oxygen density of the room air used by the combustor is determined by comparing the ion current value stored in the memory with ion current values which are successively provided by the sensing device. An output signal produced thereby is utilized to control circuit elements including a fuel supplying electromagnetic pump and a combustion air blower used for supplying room air into the combustor.

4 Claims, 9 Drawing Figures

OXYGEN DENSITY DETECTING DEVICE IN COMBUSTOR

BACKGROUND OF THE INVENTION

The present invention relates to a device for detecting the oxygen density of room air or the like by detecting an ion current in a combustor.

The oxygen density of the air in the room where a heating apparatus or a water heater with an open type combustor using indoor air for combustion is installed is an essential factor for safety and health. Therefore, it is necessary to detect the oxygen density of the air in such a room and to stop the combustor or to ventilate the room if necessary.

As shown in FIG. 1, the ion current value of flames in an open type combustor decreases with the oxygen density of air in the room. Therefore, the oxygen density of air in the room can be detected by detecting the flame ion current. For instance, the device may be constructed such that a reference level is suitably set and the reference level is compared with each of the ion current levels which are provided successively. When the ion current level is lower than the reference level, an output signal is generated to detect the oxygen density of the air in the room.

However, if the same reference value is used for more than one open type combustor, the oxygen density cannot be detected with a high accuracy because the ion currents of the open type combustors are not always equal to one another due to variations in characteristics which occur during manufacture or changes with time. Therefore, the relationships between ion current and oxygen density of the combustors are different.

This will become more apparent from the following description. It is assumed that first and second open type combustors A and B have different ion current characteristics with time as shown in FIG. 2. If, in this case, the common reference level for the combustors A and B is set to the level a indicated in FIG. 2, while in the combustor A an oxygen density of about 18% is detected, in the combustor B the oxygen density about 18.5%. Thus, the oxygen density cannot be accurately detected with plural combustors if a single reference level is used.

If the reference level for the first open type combustor A is set to the level a and the reference level for the second combustor B is set to the level b as shown in FIG. 2, then the oxygen density of the room air can be detected with a high accuracy. Therefore, a method may be advantageously used in which characteristics of ion current level with time are obtained for a plurality of open type combustors by prior tests, and reference levels set for each combustor separately.

However, that method still involves drawbacks in that it is cumbersome and expensive to test a large number of manufactured open type combustors one by one to obtain the individual reference values.

SUMMARY OF THE INVENTION

Accordingly, an object of the invention is to eliminate the above-described difficulties.

In accordance with this and other objects of the invention, there is provided an oxygen density detecting device for a combustor including memory means for storing an ion current value a predetermined period of time after the formation of flame in the combustor and means for determining an oxygen density of room air used for combustion by comparing the ion current value stored in the memory means with ion current values which are successively provided from the combustor.

The detecting device of the invention can be manufactured at a low cost and can detect the oxygen density of room air or the like with a high accuracy.

The foregoing object and other objects of the invention will become more apparent from the following detailed description when read in conjunction with the accompanying drawings.

BRIEF DESCRIPTION OF THE DRAWINGS

In the accompanying drawings:

FIG. 3 through FIG. 5B show a heating apparatus to which a detecting device according to the invention is applied, of which FIG. 3 is an explanatory diagram showing the arrangement of the heating apparatus, FIG. 4 is an explanatory diagram showing the construction of an open type combustor used in the heating apparatus, FIG. 5B is a drive circuit of a second relay coil;

DESCRIPTION OF THE PREFERRED EMBODIMENTS

Figure 1:
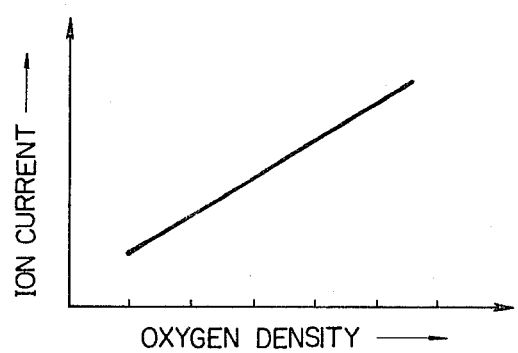
FIG. 1 is a graphical representation indicating a characteristic of flame ion current value with oxygen density.
Figure 2:
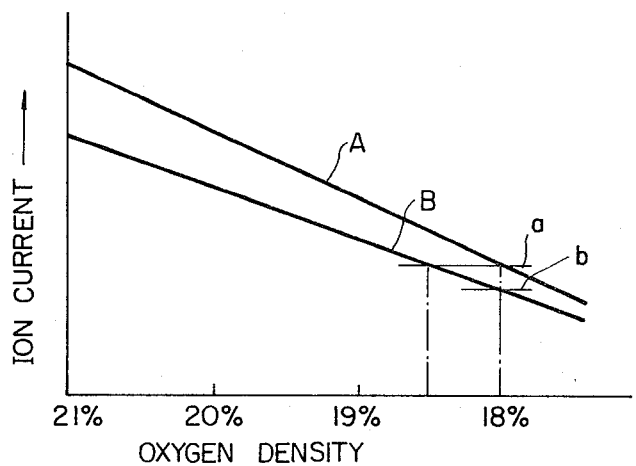
FIG. 2 is also a graphical representation indicating characteristics of flame ion current with oxygen density used for a description of drawbacks accompanying a conventional oxygen density detecting operation with open type combustors.
Figure 3:
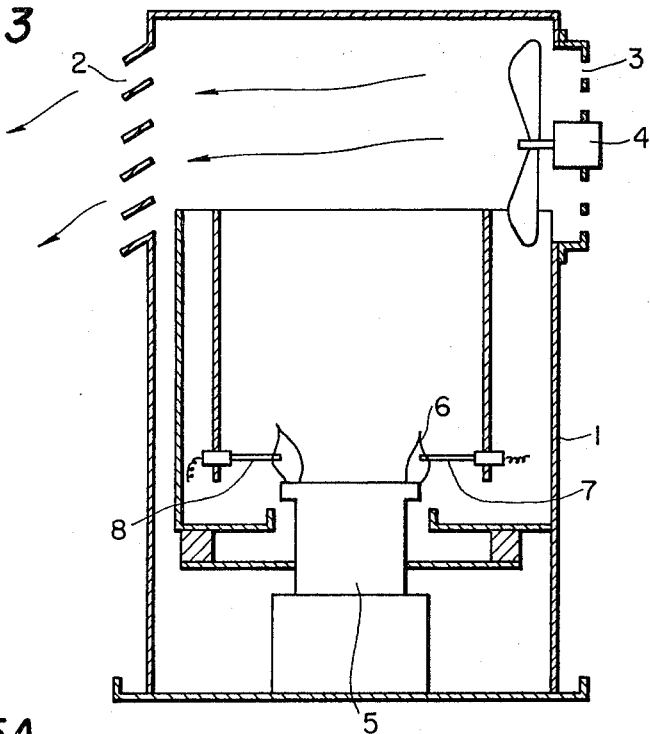
Figure 4:
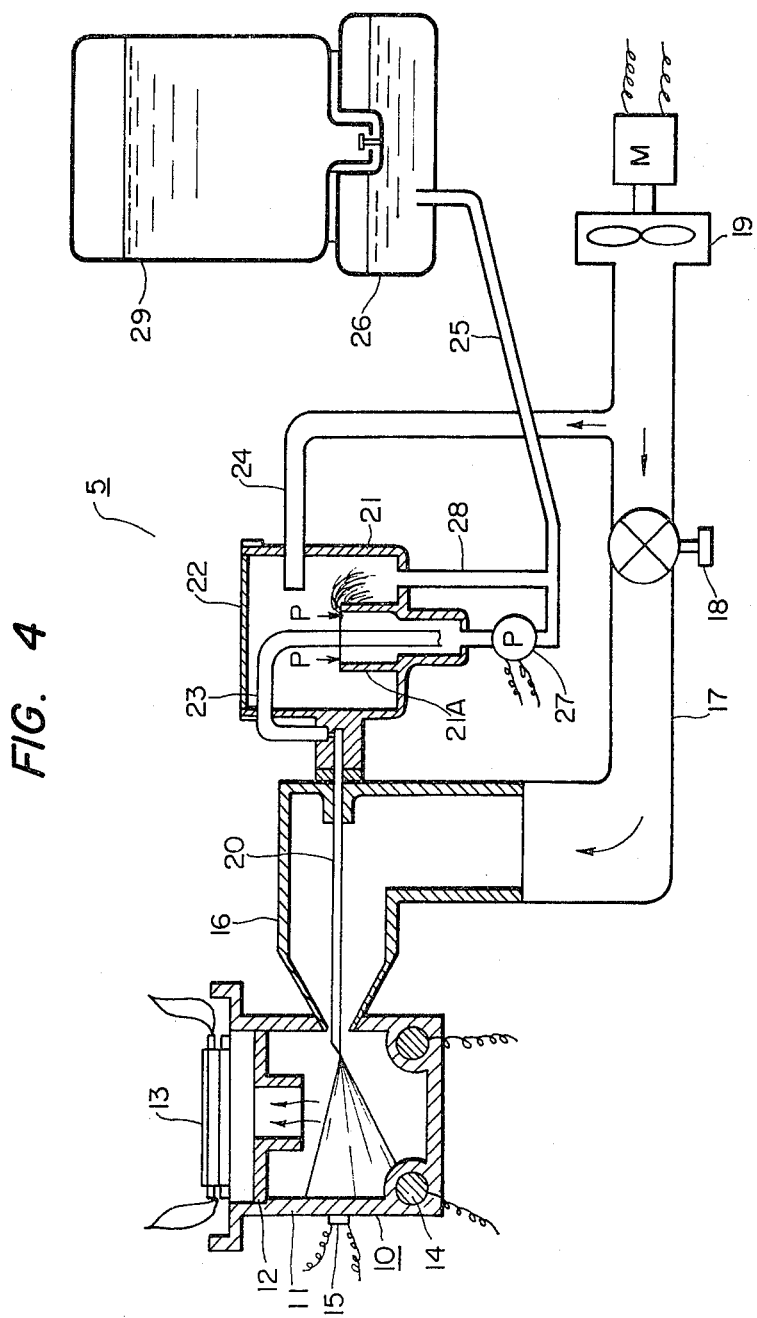

A preferred embodiment of a detecting device constructed according to the invention will be described as by way of example applied to a heating apparatus having an open type combustor which has a construction and an electrical circuit as shown in FIGS. 3 through 5, the open type combustor using room air for combustion. First, the construction and electrical circuit of the heating apparatus will be described.

FIG. 3 is an explanatory diagram showing the construction of the heating apparatus. In FIG. 3, reference numeral 1 designates an outer casing, 2 hot air blow-off openings formed in the upper portion of the front wall of the outer casing 1, 3 designates air suction holes formed in the upper portion of the rear wall of the outer casing 1, 4 a hot air blowing fan mounted in the region of the air suction holes 3, 5 the aforementioned combustor provided in the lower portion of the interior of the outer casing 1, 6 flame formed by the combustor 5, 7 a flame rod for detecting a flame current, and 8 an ignition unit.

FIG. 4 is a schematic diagram showing the arrangement fo the combustor 5. In FIG. 4, reference numeral 10 designates a burner, 11 a carburetor cylinder, 12 a throttle plate, 13 a burner head, and 14 a heater for heating the inner wall of the carburetor cylinder 12. The heater 14 is formed with a resistor having a positive temperature resistance characteristic, hereinafter referred to as "a PTC thermistor" when applicable, buried circularly in the wall of the carburetor cylinder.

Further in FIG. 4, reference numeral 15 designates a temperature detecting element for detecting the temperature of the carburetor cylinder 12, the element being constituted by a PTC thermistor whose resistance increases abruptly when the temperature of the wall of the carburetor cylinder 11 reaches about 250° C., 16 a nozzle coupled to the carburetor cylinder 11, 17 an air duct connected to the nozzle 16, 18 a control valve for controlling the flow rate of blowing air, 19 a combustion air blower for blowing indoor air for combustion, and 20 a needle provided coaxially in the straight portion of the nozzle 16. One end of the needle extends through the opening on the burner side of the nozzle into the carburetor cylinder 11 while the other end extends through the wall of the nozzle opposite to the aforementioned opening of the nozzle 16.

Further in FIG. 4, reference numeral 21 designates an oil leveler with a lid 22 and a substantially inverted-U-shaped orifice tube which has one end extending into the fuel pool in the oil leveler and the other end connected to the needle 20, 24 designates a static pressure tube having one end extending into the oil leveler 21 and the other end connected to the air duct 17, 25 an oil supplying pipe having one end connected to the bottom of the oil leveler 21 and the other end connected to an auxiliary tank 26, 27 an oil supplying electromagnetic pump disposed in the oil supplying pipe 25, 28 a returning pipe connected between the bottom of the oil leveler 21 and the midpoint of the oil supplying pipe 25, and 29 a tank for storing liquid fuel.

Figure 5A:
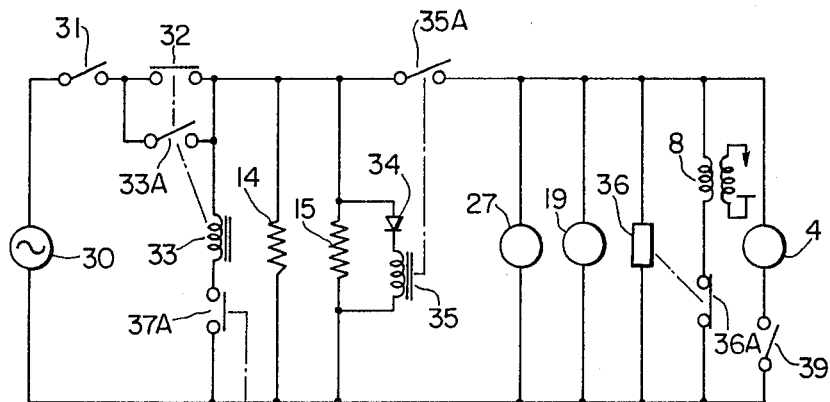
FIG. 5A is an electrical circuit of the combustor.

FIG. 5A is an electrical circuit of the heating apparatus thus constructed. In FIG. 5A, reference numeral 30 designates a commercial power source, 31 a main switch, 32 a first push-button type switch, 33 a first relay coil, 33A a normally open contact of the first relay coil 33 with the contact 33A being connected in parallel with the first push-button type switch 32, 37A a normally closed contact of a second relay coil 37 which is connected in series with the first relay coil 33 and is driven by the detecting device of the invention, 14 the aforementioned heater, 15 the aforementioned temperature detecting element, and 34 and 35 a diode and a third relay coil, respectively, which are connected in parallel with the temperature detecting element 15. Even after the current applied to the third relay coil 35 is decreased, the third relay coil is operated.

Further in FIG. 5A, reference character 35A designates a normally open contact of the third relay coil 35, 27 and 19 are the aforementioned air supplying electromagnetic pump and combustion air blower, respectively, 36 is a timer unit, 36A a normally closed contact of the timer unit, 8 the aforementioned ignition unit, 4 the above-described hot air blowing fan, and 39 a normally open delay switch which is closed after combustion starts.

Figure 5B:
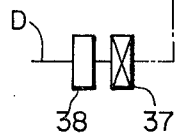

FIG. 5B shows a drive circuit for the second relay coil 37 which is driven by the device of the invention. In FIG. 5B, reference numeral 38 designates a driver which drives the second relay coil 37 when the output signal of the device of the invention is applied thereto. A power source for the circuit is not shown.

Figure 6:
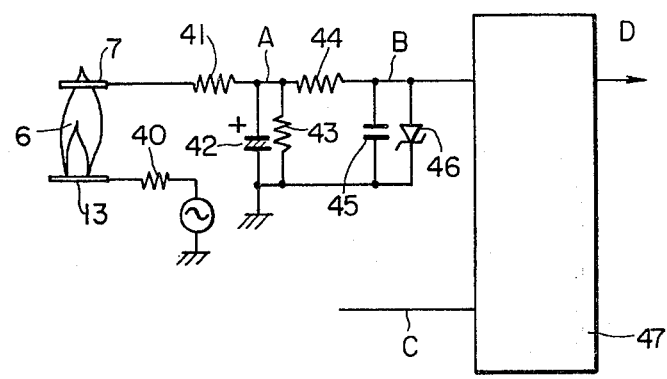
FIG. 6 is a circuit diagram showing an example of a detecting device according to the invention.
Figure 8:
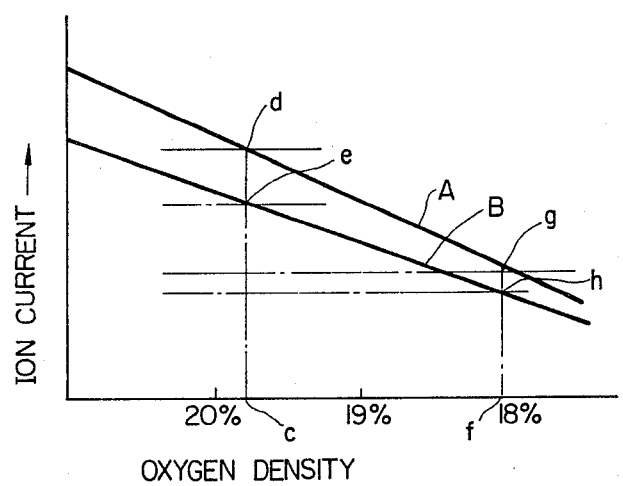
FIG. 8 is a graphical representation showing characteristics of ion current with oxygen density in the detecting device according to the invention.
Figure 7:
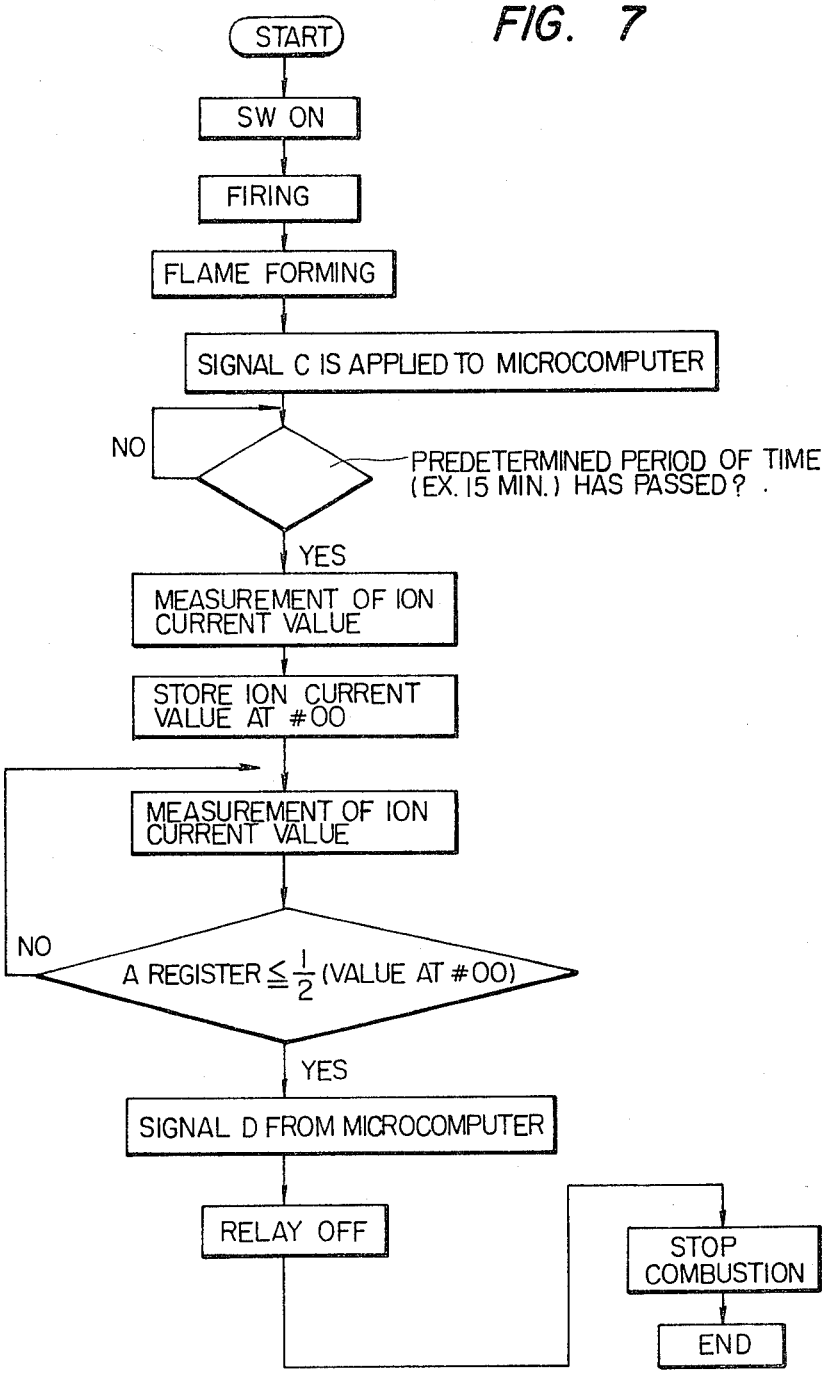
FIG. 7 is a flow chart for a description of the operation of the detecting device of the invention.

FIG. 6 shows a specific example of the detecting device of the invention. FIG. 7 is a flow chart for a description of the operation of the detecting device. FIG. 8 is a graphical representation indicating a characteristic of ion current with oxygen density.

In FIG. 6, reference numeral 7 designates the aforementioned flame rod serving as the ion current detecting sensor, 13 the aforementioned burner head to which alternating current is applied through a first resistor 40 and with the alternating current being further applied through the flame to the flame rod 7, 41 a second resistor connected to the flame rod 7, 42 a smoothing capacitor for smoothing a ripple component of the ion current (although the ion current is rectified by the flame), 43 a resistor for converting an ion current into a voltage signal, 44 a protective resistor, 45 a capacitor, 46 a Zener diode, and 47 a microcomputer serving as a memory device and an oxygen density determining device. The protective resistor 44, the capacitor 45 and the Zener diode 45 serve to protect the microcomputer from the application of overvoltage. The microcomputer 47 may be an M58844P type microcomputer manufactured by Mitsubishi Electric Co., Ltd. of Japan.

The operation of the detecting device of the invention will be described with reference to FIGS. 3 through 8. When the push-button type switch 32 is turned on after the main switch 31 has been turned on (FIG. 5A), current is applied to the first relay coil 33 to cause the normally open contact 33A to close because the normally closed contact 37A of the second relay coil 37 is maintained closed. Therefore, even if the push-button type switch 32 is released thereafter, current remains applied to the heater 14 made up of the PTC thermistor and to the temperature detecting element 15 in the rear stage of the switch 32.

When current is applied to the heater 14, the inner wall of the carburetor cylinder 11 is heated. When the temperature of the inner wall of the carburetor cylinder 11 reaches about 250° C., the resistance of the temperature detecting element 15 including the PTC thermistor for detecting the temperature of the carburetor cylinder 11 is increased. As a result, the third relay coil 35 short-circuited by the temperature detecting element 15 is driven to close the normally open contact 35A thereof. Upon closure of the contact 35A, current is applied to the fuel supplying electromagnetic pump 27, the combustion air blower 19, the timer unit 36 and the ignition unit 8.

While the blower 19 is operated, room air is injected, as combustion air into the carburetor cylinder 11 through the air duct 17 and the nozzle 16. A part of the combustion air is supplied to the oil leveler 21 through the air duct 17 and the static pressure tube 24. Further, as the electromagnetic pump 27 is driven, the liquid fuel supplied into the auxiliary tank 26 from the tank 29 is applied through the oil supplying pipe 25 into the oil leveler 21. The liquid fuel supplied into the oil leveler 21 overflows when its level reaches the top of a partition in the oil leveler and returns to the oil supplying pipe 25 through the return pipe 28. The liquid fuel thus returned is pumped up by the electromagnetic pump 27. the fuel consumed during combustion is supplemented from the tank 29. Thus, the level of the fuel in the oil leveler is maintained constant.

In this operation, air is supplied into the oil leveler 21 through the static pressure return tube 24. Therefore, air pressure is applied to the surface of the fuel in the oil leveler 21 so that fuel is supplied to the needle 20 through the orifice tube 23. As the combustion air is jetted through the nozzle 16, the fuel supplied to the needle 20 is atomized by the shear force of the jetted air and spread conically into the carburetor cylinder 11 where it is heated and gasified.

The fuel thus treated mixes with the combustion air to form a mixture. The mixture is concentrated at the hole of the throttle plate 12 where the mixture density is made uniform. Then, the mixture is jetted through the hole of the throttle plate 12.

During this operation, the ignition unit 8 is energized to ignite the mixture by the ignition unit 8, thus forming flame in the combustor 5.

When combustion starts in this way, the delay switch 39 is closed to operate the hot air supplying blower 4. As a result, indoor air is sucked into the outer casing 1 through the air suction holes 3 and is heated by the flames 6. The air thus heated is returned to the room to increase the temperature of the air in the room.

Substantially simultaneously with the operation of the hot air supplying blower 4, the normally closed contact of the timer unit 36 is opened to interrupt the application of current to the ignition unit 8.

During combustion, the inner wall of the carburetor cylinder 11 is kept warm by the heat of combustion. Therefore the temperature of the inner wall is maintained at a predetermined value without using the heater 14. Under this condition, the resistance of the heater 14 including the PTC thermistor is increased thereby decreasing the current flowing therein as a result of which the generation of heat is suspended. Thus, the inner wall of the carburetor cylinder 11 is maintained at the predetermined temperature of about 250° C.

The heating operation can be stopped by opening the main switch 31.

Next, the operation of the detecting device of the invention will be described. When the main switch 31 is turned on, the power switch (not shown) of the detecting device is also turned on. Therefore, the combustor performs the ignition operation as described above forming flame therein, whereupon an ion current is generated between the burner head 13 and the flame rod 7. The ion current is converted into a voltage signal A by the third resistor 43. The voltage signal A is changed into a voltage signal B via the protective resistor 44 with the voltage signal B being applied to the microcomputer 47. On the other hand, simultaneously with the start of combustion, a signal C is applied to the microcomputer 47 to commence a time counting operation. When a predetermined period of time, for instance, fifteen minutes, during which the flame ion current stabilizes has passed, the microcomputer stores at address #00 in a memory therein the ion-current determined voltage at that time instant. The ion-current determined voltage inputted into an A register from the flame rod is compared with the ion-current determined voltage thus stored in the microcomputer.

When the oxygen density of the air in the room is decreased by the combustion to the extent that the ion-current determined voltage in the A register is less than half of the stored ion-current determined voltage, the microcomputer 47 provides an output signal D.

Upon provision of the output signal D, the second relay coil 37 is driven by the driver 38 causing the normally closed contact 37A to open. When the contact 37A is opened, the application of current to the circuit elements such as the heater 14 and the pump 27 is suspended and hence combustion is stopped. Thus, the room air oxygen density is detected and combustion halted when it becomes dangerously low.

It is assumed that first and second open type combustors A and B having different characteristics of ion current with time as shown in FIG. 8 are provided. In this case, as the oxygen density corresponding to the ion-current determined voltage stored in the microcomputer 47 is that of combustion air (or room air) at the predetermined period of time after the start of combustion, the oxygen density is constant even though different ion-current determined voltages are stored separately for the different combustors. Furthermore, as the characteristic of ion current value with time is substantially represented by a straight line, the oxygen density in the room as combustion progresses is accurately detected merely by comparing ion-current determined voltages provided continuously with the stored ion-current determined voltage which is used as a reference voltage.

In FIG. 8, reference character c designates the time instant that an ion-current determined voltage is stored, d and e, the ion-current determined voltages of the open type combustors A and B which are detected at the time instant c, f the time instant that the oxygen density of indoor air is detected, and g and h halves of the ion-current determined voltages d and e which are detected and stored.

A preferred embodiment has been described with reference to a case where the oxygen density of room air is detected, However, the technical concept of the invention can be similarly applied to a case where the presence or absence of flame in the combustor is detected.

In the above-described embodiment, the output signal D of the detecting device constructed according to the invention is used to stop the operations of the pump 27, the blower 19, etc. which are required for combustion thereby to stop the combustion air. However, the output signal D may be utilized in such a manner that a lamp is turned on by the output signal D to warn the user of a low oxygen density and then the combustion is stopped manually by the user. That is, a variety of methods of utilizing the output signal D can be used.

The preferred embodiment has been described with reference to the case where the detecting device of the invention is applied to a combustor which is operated in a closed room. However, the detecting device of the invention is applicable to any heating unit such as a water heater with an open type combustor. The invention can be applied not only to a heating apparatus using liquid fuel but also to a heating apparatus using gas fuel.

As is clear from the above description, the oxygen density detecting device for a combustor of the invention includes memory means for storing the ion current value the predetermined period of time after the formation of flame in the combustor, and the determining means for determining the oxygen density by comparing the ion current value stored in the memory means with ion current values which are provided successively. With this construction, the detecting device of the invention can be manufactured at a low cost and can detect the oxygen density of room air or the like with a high accuracy.

According to the invention, an ion current value is stored when it is substantially stabilized. Therefore, the oxygen density of room air or the like can be detected more accurately.

Furthermore, according to the invention, the output signal of the determining means is utilized to control the operations of the circuit elements required for combustion. Therefore, even if the user is not aware of the decrease of the oxygen density in the room, he will be protected from oxygen deficiency.

What is claimed is:

1. An oxygen density detecting device for a combustor, which detects an ion current of flame to detect an oxygen density of air for combustion, comprising:

means for applying a reference current through said flame;

means for sensing an ion current in said combustor by detecting a voltage produced across said flame by said reference current;

memory means coupled to said sensing means for storing as a reference value an ion current value sensed by said sensing means a predetermined period of time after a flame is formed in said combustor;

means for determining and producing an output signal representing an oxygen density of air used for combustion by comparing said reference value stored in said memory means with ion current values subsequently and successively provided by said sensing means; and means for controlling at least one of an electromagnetic pump for supplying fuel to said combustor and a combustion air blower for supplying air to said combustor in response to said output signal.

2. The device as claimed in claim 1, wherein said predetermined period of time is sufficiently long for said ion current to have substantially stabilized.

3. The device as claimed in claim 1, in which said combustor utilizes room air for combustion and wherein said detecting device detects an oxygen density of room air.

4. The device as claimed in claim 1, wherein said controlling means comprises means for shutting off said pump and said blower when said output signal is at a level indicative of a predetermined oxygen density or an oxygen density less than said predetermined oxygen density.

* * * * *